United States Patent [19]

Brusis et al.

[11] Patent Number: 4,517,621
[45] Date of Patent: May 14, 1985

[54] CIRCUIT ARRANGEMENT FOR THE PRODUCTION OF A QUASI-ELECTROSTATIC FIELD

[76] Inventors: Otto Brusis, Mühlehen 13, 7744 Königsfeld; Sigurd Maiter, Bismarckring 38, 7900 Ulm; Paul Haufe, Südring 10, 8878 Bibertal-Anhofen, all of Fed. Rep. of Germany

[21] Appl. No.: 421,784

[22] Filed: Sep. 23, 1982

[30] Foreign Application Priority Data

Aug. 11, 1982 [DE] Fed. Rep. of Germany ....... 3229821

[51] Int. Cl.$^3$ ............................................. H01T 20/02
[52] U.S. Cl. .................................................. 361/231
[58] Field of Search .............. 361/230, 231, 233, 235; 128/419 N, 371, 362

[56] References Cited

U.S. PATENT DOCUMENTS

| 3,292,042 | 12/1966 | Michener et al. | 361/231 X |
| 3,678,337 | 7/1972 | Grauvogel | 361/231 |
| 3,721,872 | 3/1973 | Sorg et al. | 361/231 |
| 3,973,927 | 8/1976 | Furchner et al. | 55/106 X |

FOREIGN PATENT DOCUMENTS 1326820  8/1973  United Kingdom ................ 128/371

Primary Examiner—Harry E. Moose, Jr.
Attorney, Agent, or Firm—Fred Philpitt

[57] ABSTRACT

There is described a circuit arrangement for the production of a quasi-electrostatic field for climatological and/or therapeutical applications which is variably set to external parameters. These external parameters may be the screening of the external natural electric field, which screening is given in dependence on the constructional design of the room to be air-conditioned, or the long-term or short-term fluctuations of the external natural electric field.

11 Claims, 1 Drawing Figure

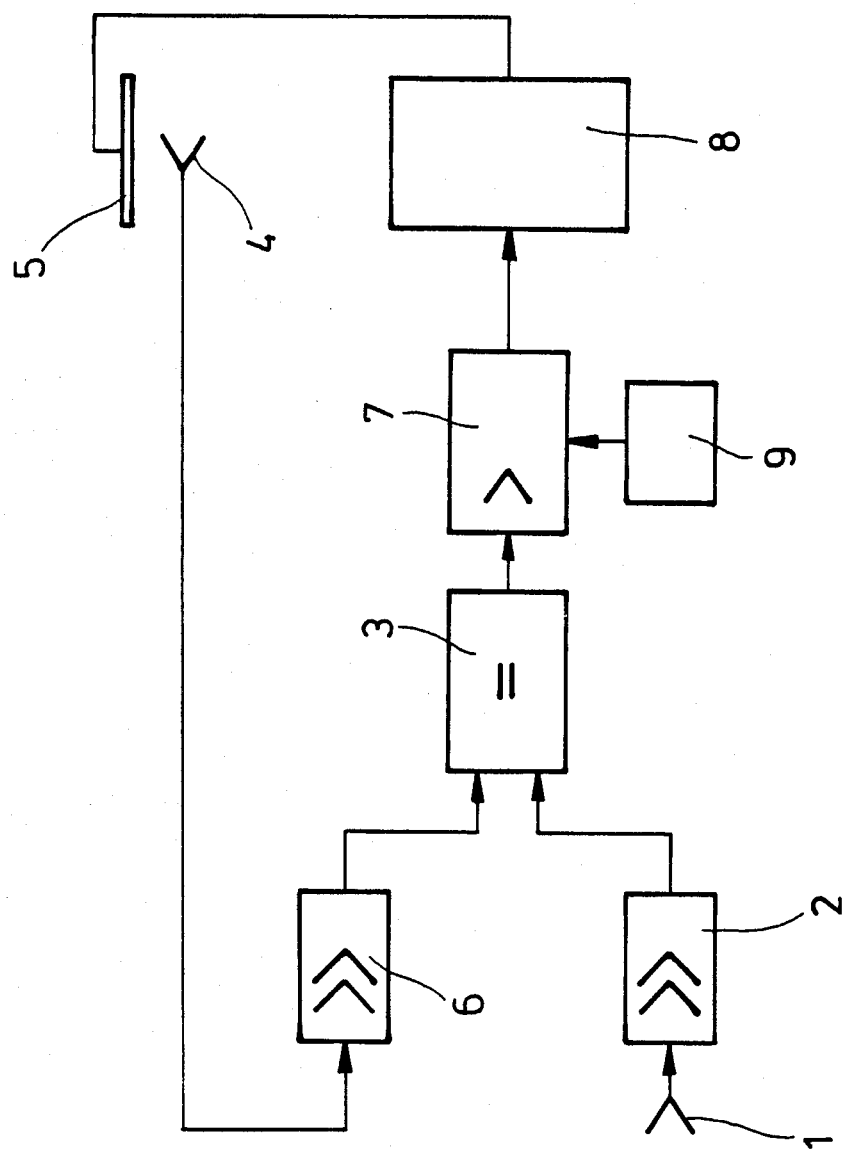

CIRCUIT ARRANGEMENT FOR THE PRODUCTION OF A QUASI-ELECTROSTATIC FIELD

The invention relates to a circuit arrangement for the production of a quasi-electrostatic field for climatological and/or therapeutical applications which comprises a high-voltage generator circuit, whose output voltage is applied to an electrode which is arranged inside the room to be air-conditioned.

A circuit arrangement of this kind is known from DE AS 29 24 945. The high voltage generated therein is independent of external parameters. This means that the field strength produced by the electric air-conditioning apparatus does not take into account, within the room to be air-conditioned, the respective constructional factors of the building. Since the weakening of the natural field varies inside closed rooms, depending on the construction, the known apparatuses do not allow the correct operating point to be predetermined for any place of use by a single setting specified by the factory. In addition, long-term fluctuations of the field strength, which occur in nature, for example, during the day cycle, are not considered at all.

It is the object of the present invention to develop a circuit arrangement of the kind indicated at the beginning in such a way that variable external parameters can be considered and that there is automatically effected an artificial field production that is adapted to the external parameters.

According to the invention, this problem is solved by (a) an internal probe for the detection of the effective electric field within the range of action of the electrode;

(b) a comparator which compares the output signal emitted by the internal probe with a reference voltage which is representative of a desired field within the range of action of the electrode;

(c) a control amplifier, to which the output signal emitted by the comparator is fed and whose output signal modulates the high-voltage generator circuit.

The field resultant which comes about by adding up the natural field (which is generally weakened in rooms) and the artificial field produced by the air-conditioner is measured by the internal probe provided for according to the invention. The value of the field detected by this internal probe can be compared with a specified field; the circuit arrangement then ensures that there is artificially added to the (still existing) natural field that field amount which is missing in order to attain the field value that is desired for therapeutical or other health reasons.

In the simplest case, the reference voltage is derived from an internal voltage source of the circuit arrangement. In this development, the circuit arrangement always brings about an adjustment to that field strength inside the room to be air-conditioned which is specified by the reference voltage and, in doing so, considers varying weakenings of the natural field which depend on the construction of the building. Expediently, the magnitude of the reference voltage is individually settable in order thus to allow the magnitude of the desired field to be adapted to the respective requirements.

If the reference voltage is derived from an external probe which is arranged outside the room to be air-conditioned and detects the natural field of the external atmosphere, then the circuit arrangement automatically brings about a re-adjustment in the internal room of the building to the natural field prevailing in the external atmosphere. In doing so, it not only considers, as mentioned above, varying weakenings of the external field caused by varying constructional factors but, over and above this, always automatically corrects the strength of the field prevailing inside the building to the natural fluctuations of the external field. In this connection, it is assumed that the healthiest long-term fluctuations of the field in which living creatures move are those which are specified by nature. The living creatures have become accustomed and have adapted to these long-term fluctuations during the course of their development over thousands of years.

Two variants are possible in the development of this last variant of the circuit arrangement:

On the one hand, the time constant of the circuit arrangement may be chosen to be such that only the slow variations in the natural field fluctuations are readjusted and that in the high-voltage generator circuit an artificial residual ripple is superimposed on the high voltage generated therein. Research has shown that a special therapeutical or health promoting effect is inherent in the residual ripple of the electric field. The described constructional form, wherein the residual ripple is artificially generated, will be primarily used in cases where specific therapeutical results are aimed at by exerting a selective influence on the residual ripple. Expediently, the time constant of the circuit arrangement is in this case greater than one second, thus causing the higher-frequency residual ripple to be no longer re-adjusted.

Alternatively, the time constant of the circuit arrangement may be chosen to be such that the ripples superimposed on the slow changes of the natural field are also re-adjusted. This constructional form will be primarily chosen when there is desired a simulation of the natural field that is as accurate as possible. Here, too, it may be assumed that, on account of the long process of acclimatisation, the natural ripples are generally also the healthiest. The time constant of the circuit arrangement should in this case be smaller than approximately 1/10 second.

There may be additionally provided a selective filter which, from the frequency spectrum of the ripple of the natural field detected by the external probe, lets through frequencies in a window having a specific position and width. By this means, there may be taken into account recent scientific findings to the effect that in the natural frequency spectrum of the ripples, too, there are contained frequencies which, under specific conditions, are less beneficial with regard to health aspects. It is also possible to determine the frequency spectrum which is taken over from the natural ripple and is adjusted to the artificially generated ripple, in order to attain specific therapeutical effects.

For this purpose, the position and the width of the filter window can advantageously be set on a programming unit.

According to another development of the invention, the circuit path associated with the external probe and the circuit path associated with the internal probe are designed so as to be asymmetrical, so that an undermodulation or an over-modulation can take place. In this way, it is possible to allow the field prevailing in the interior of the building to follow the external natural field, but the magnitude thereof may differ by a specific amount. This can expediently be achieved in that a preamplifier is respectively connected between the probes and the comparator, the amplification factors of the two amplifiers being settable independently of each other.

An exemplified embodiment of the invention will hereinafter be explained in more detail with reference to the drawing, the single figure of which shows the circuit arrangement for an electrostatic air-conditioner.

In the drawing, the reference symbol 1 denotes a probe for electric fields which is put up in the free atmosphere, in other words at a point at which the natural quasi-electrostatic fields are not screened or changed by constructional measures. The probe 1 will therefore hereinafter be called the "external probe". For this purpose, there may be used a standard apparatus which operates according to the influence principle (for example corresponding to types Q 475/A, Q 475/C of Eltex Elektrostatic GmbH, 7858 Weil am Rhein) or according to a measurement principle where the current generated by an ionising radiation is measured (Type EMO1 of the afore-mentioned manufacturer).

The output signal emitted by the external probe 1 is amplified in a pre-amplifier 2 and is then fed to an input of a comparator 3.

Another probe 4 is arranged inside the room to be air-conditioned, within the range of action of the electrode 5 to which there is applied the high voltage generated by the circuit arrangement and co-determining the electric internal field. It is consequently called the "internal probe" and may be basically similar in construction to the external probe 1. The output signal emitted by the internal probe 4 is fed via a pre-amplifier 6, which corresponds to the amplifier 2, to the second input of the comparator 3.

The comparator 3 compares the output signals from the probes 1 and 4 and thus, in the final analysis, the field prevailing in the room to be air-conditioned with the natural field in the free atmosphere. If the magnitude of one field differs from that of the other field, then the comparator 3 produces an output signal indicating the difference, which signal is fed to a control amplifier 7.

The control amplifier 7 output voltage modulates the high-voltage generator circuit 8 of the electrostatic air-conditioner, for example in that it is used as the primary voltage of a cascade connection. By this means, the high-voltage generator circuit 8 applies a variable voltage to the electrode 5 in such a way that the electrostatic or quasi-electrostatic field produced by the electrode 5 follows the natural external field detected by the external probe 1. In this way, all the natural field variations can be replicated by the electrostatic air-conditioner in the interior of the room to be air-conditioned.

As regards the field variations, one has to distinguish between the relatively slow quasi-continuous ripples, which occur, for example, within a day cycle, and the relatively fast ripples which are superimposed on the slow variations. As research has shown, it is precisely the magnitude and the frequency of these ripples which contribute to a considerable extent to the (positive or negative) healthwise effect of the electrostatic field.

The afore-described circuit may be so constructed that only the slow quasi-continuous variations of the external field are replicated by the high-voltage generator circuit 8, whereas the therapeutically important voltage ripples are artificially generated on the electrode 5 in known manner. For this purpose, the entire circuit construction is given an effective time constant which is approximately in the region of a second or thereabove.

However, it is also conceivable to provide the entire circuit arrangement with a time constant which is so small, for example in the region of a tenth of a second or less, that it is capable of re-adjusting at least also the low-frequency ripples of the natural field and of transmitting them to the voltage applied to the electrode 5. In such a case, it may be recommendable to integrate a selective band-pass filter into the control amplifier 7. The window position and the window width of this filter are determined in accordance with the scientific findings about the healthwise effect of the different ripple frequencies. It is particularly favourable to make the filter variable in design, allowing the window position and the window width to be individually set by the programming unit 9 according to the therapeutical purposes.

It is of course not necessary to simulate identically the external field detected by the external probe 1. For example, depending on the geographical conditions, it may be appropriate to simulate the natural external field in an amplified or weakened manner in the room to be air-conditioned. For this purpose, the two circuit branches associated with the external and internal probes have to be designed so as to be asymmetrical, for example in that different amplification factors are given to the two pre-amplifiers 2, 6.

In the simplest case, the signal given by the external probe 1 can be completely dispensed with. Instead, there is then fed to the comparator 3 a reference voltage which corresponds to a specific desired field in the room to be air-conditioned. In this connection, there has to be taken into account the fact that, depending on the constructional factors, the natural external field is weakened in the room interior to a varying degree. The probe 4, which measures the sum of the (weakened) natural field and of the artificially produced field, then causes the electrostatic air-conditioner to complement the respective weakened field to the therapeutically effective value that is specified by the reference voltage.

We claim:

1. A circuit arrangement for the production of a quasi-electrostatic field for climatological and/or therapeutical applications which comprises a high-voltage generator circuit whose output voltage is applied to an electrode arranged inside the room to be air-conditioned, comprising in combination:
    (a) an internal probe for the detection of the effective electric field within the range of action of the electrode,
    (b) a comparator which compares the output signal emitted by the internal probe with a reference voltage which is representative of a desired field within the range of action of the electrode, and which voltage is derived from an external probe which is arranged outside the room to be air-conditioned and detects the natural field of the external atmosphere, and
    (c) a control amplifier to which the output signal emitted by the comparator is fed and whose output signal modulates the high voltage generator circuit.

2. A circuit arrangement as claimed in claim 1, characterised in that the reference voltage is derived from an internal voltage source of the circuit arrangement.

3. A circuit arrangement as claimed in claim 2, characterised in that the magnitude of the reference voltage is individually settable.

4. A circuit arrangement as claimed in claim 1, characterised in that the time constant of the circuit arrangement is chosen to be such that only the slow variations of the natural field are re-adjusted and in that in the high-voltage generator circuit (8) an artificial residual ripple is superimposed on the high-voltage generated therein.

5. A circuit arrangement as claimed in claim 4, characterised in that the time constant is greater than one second.

6. A circuit arrangement as claimed in claim 1, characterised in that the time constant of the circuit arrangement is chosen to be such that the ripples superimposed on the slow variations of the natural field are also re-adjusted.

7. A circuit arrangement as claimed in claim 6, characterised in that the time constant is smaller than 1/10 second.

8. A circuit arrangement for the production of a quasi-electrostatic field for climatological and/or therapeutical applications which comprises a high-voltage generator circuit whose output voltage is applied to an electrode arranged inside the room to be air-conditioned, which comprises:
 (a) an internal probe (4) for the detection of the effective electric field within the range of action of the electrode (5);
 (b) a comparator (3) which compares the output signal emitted by the internal probe (4) with a reference voltage which is representative of a desired field within the range of action of the electrode;
 (c) a control amplifier (7), to which the output signal emitted by the comparator (3) is fed and whose output signal modulates the high-voltage generator circuit (8);
 said reference voltage being derived from an external probe (1) which is arranged outside the room to be air-conditioned and detects the natural field of the external atmosphere,
 the time constant of the circuit arrangement being chosen to be such that the ripples superimposed on the slow variations of the natural field are also re-adjusted, and
 (d) a selective filter which, from the frequency spectrum of the ripple of the natural field detected by the external probe (1), lets through frequencies in a window having a specific position and width.

9. A circuit arrangement as set forth in claim 8 wherein the position and the width of the filter window are settable on a programming unit (9).

10. A circuit arrangement for the production of a quasi-electrostatic field for climatological and/or therapeutical applications which comprises a high-voltage generator circuit whose output voltage is applied to an electrode arranged inside the room to be air-conditioned, which comprises:
 (a) an internal probe (4) for the detection of the effective electric field within the range of action of the electrode (5),
 (b) a comparator (3) which compares the output signal emitted by the internal probe (4) which a reference voltage which is representative of a desired field within the range of action of the electrode; and
 (c) a control amplifier (7) to which the output signal emitted by the comparator (3) is fed and whose output signal modulates the high-voltage generator circuit (8),
 said reference voltage being derived from an external probe (1) which is arranged outside the room to be air-conditioned and detects the natural field of the external atmosphere,
 the circuit branch associated with the external probe (1) and the circuit branch associated with the internal probe (4) being designed so as to be asymmetrical so that an under-modulation or an over-modulation can take place.

11. A circuit arrangement as claimed in Claim 10 characterized in that between the probes (1, 4) and the comparator (3) there is connected a pre-amplifier (2, 6); the amplification factors of the two amplifiers (2, 6) being settable independently of each other.

* * * * *